United States Patent
Hung et al.

(10) Patent No.: US 11,648,349 B2
(45) Date of Patent: May 16, 2023

(54) INJECTION DEVICE FILL VOLUME MANAGEMENT

(71) Applicant: Owen Mumford Ltd., Oxfordshire (GB)

(72) Inventors: Andrew Hung, Oxfordshire (GB); Abiodun Falodi, Oxfordshire (GB); Robert Dutton, Oxfordshire (GB); Marco Caglio, Oxfordshire (GB); Andreas Artelsmair, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 627 days.

(21) Appl. No.: 16/585,716

(22) Filed: Sep. 27, 2019

(65) Prior Publication Data
US 2020/0101228 A1 Apr. 2, 2020

(30) Foreign Application Priority Data
Sep. 28, 2018 (GB) .................................... 1815825

(51) Int. Cl.
*A61M 5/20* (2006.01)
*A61M 5/24* (2006.01)
*A61M 5/315* (2006.01)

(52) U.S. Cl.
CPC ............ *A61M 5/2033* (2013.01); *A61M 5/24* (2013.01); *A61M 5/31533* (2013.01); *A61M 5/31576* (2013.01)

(58) Field of Classification Search
CPC ........ A61M 5/2033; A61M 2005/3152; A61M 2005/31518; A61M 5/315; A61M 5/3158;
(Continued)

(56) References Cited

U.S. PATENT DOCUMENTS 5,318,547 A * 6/1994 Altschuler ............ A61M 5/315
604/263
2006/0237597 A1 10/2006 D'Andria
(Continued)

FOREIGN PATENT DOCUMENTS

WO 2016/118688 A1 7/2016
WO 2018/167498 A1 9/2018

OTHER PUBLICATIONS

Extended European Search Report issued in European Patent Application No. 19199947.3 dated Dec. 2, 2019.

*Primary Examiner* — Bhisma Mehta
*Assistant Examiner* — Nidah Hussain
(74) *Attorney, Agent, or Firm* — Quarles & Brady LLP

(57) ABSTRACT

An injection device including: a body including a syringe locator for receiving a syringe; and a firing mechanism including a rear cap, a plunger configured to be axially displaced in a forward direction relative to the rear cap and a driver system for driving the plunger forwards upon activation of the injection device, the firing mechanism configured to be directly or indirectly connected to the body such that an axial spacing of the rear cap and a barrel of the syringe is fixed during operation of the injection device, wherein, the firing mechanism and/or the body include first and second connection features allowing adjustment of a relative axial position of the firing mechanism and the syringe locator during assembly of the injection device.

23 Claims, 5 Drawing Sheets

(58) Field of Classification Search
CPC .......... A61M 5/31576; A61M 5/31533; A61M 5/24; A61M 5/28
USPC ........................................................ 604/136
See application file for complete search history.

(56) References Cited

U.S. PATENT DOCUMENTS

| | | |
|---|---|---|
| 2008/0262436 A1 | 10/2008 | Olson |
| 2013/0046238 A1 | 2/2013 | Edhouse et al. |
| 2016/0331905 A1* | 11/2016 | Aneas ................. A61M 5/3234 |

* cited by examiner

INJECTION DEVICE FILL VOLUME MANAGEMENT

CROSS-REFERENCE TO RELATED APPLICATIONS

The present application relates to and claims priority benefits from British Patent Application Serial No. 1815825.3, filed Sep. 28, 2018, and entitled "INJECTION DEVICE FILL VOLUME MANAGEMENT" the contents of which are incorporated herein by reference in their entirety.

TECHNICAL FIELD

The invention relates to injection devices for delivering a fluid substance to a user or patient via a syringe. In specific arrangements, the invention relates to, but need not be limited to, auto-injectors for delivering the fluid under a force applied by a drive system.

BACKGROUND

Injection devices are used for the convenient administration of medicaments to patients. For example, injection devices, which may be auto-injectors, may be used for providing a single metered dose of a medicament. Such devices may be either single use "disposable" devices in which the device is typically provided with a syringe already installed, and which is not user-replaceable, or "reusable" devices that allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an auto-injector device, in which delivery of the medicament is automated and the device may also be arranged to automate the insertion of a needle into the skin prior to the delivery of the medicament. However, it is noted that the term auto-injector may encompass injection devices that automatically insert the needle and devices which require the user to manually insert the needle.

Injection devices generally comprise a firing mechanism that is arranged to deliver a fluid from the syringe automatically under the force of a drive system, such as a drive spring. Optionally, injection devices may also comprise an insertion mechanism to displace the syringe within a housing of the injection device to cause needle penetration. The delivery arrangement generally acts via a plunger which includes a plunger and may also include or engage a piston (also referred to as a "bung") which is slidably provided within the syringe.

Injection devices may be designed and manufactured to accommodate different syringes. This provides a device that may be adapted to carry and operate syringes with different features and/or characteristics, such as different fill volumes. It is desirable to improve the safety and operability of such devices.

SUMMARY

Different syringes may be filled with different volumes of fluid, such as medicament. A difference in fill volume of a syringe results in a different axial position of the bung prior to use of the syringe as it is the bung that sets the useable volume within the barrel of the syringe. A different axial position of the bung prior to use of the syringe may also be as a result of a differently dimensioned syringe barrel. The inventors have realised that where a gap exists between an end of the plunger and the bung, e.g. because the fill volume is relatively low or the syringe barrel has a relatively large diameter, the plunger moves in free space for a distance before engaging the bung. This movement in free space can cause the plunger to accelerate to velocities that are too high, such that when the plunger contacts the bung, damage may be caused to the syringe and discomfort may be caused to the recipient of an injection.

Methods and apparatus disclosed herein may be arranged to mitigate or solve one or more problems associated with the art, including those mentioned above and/or elsewhere herein.

According to the invention in an aspect, there is provided an injection device comprising: a body comprising a syringe locator for receiving a syringe; and a firing mechanism comprising a rear cap, a plunger configured to be axially displaced in a forward direction relative to the rear cap and a driver system for driving the plunger forwards upon activation of the injection device, the firing mechanism configured to be directly or indirectly connected to the body such that an axial spacing of the rear cap and a barrel of the syringe is fixed during operation of the injection device, wherein, the firing mechanism and/or the body comprise first and second connection features allowing adjustment of a relative axial position of the firing mechanism and the syringe locator during assembly of the injection device.

The ability to alter relative axial position of the firing mechanism and the syringe locator alters the relative axial position of a forward end of the plunger and a bung located within the syringe. The relative axial position may be controlled to minimise an axial distance between the forward end of the plunger and the bung based, for example, on fill volume of the syringe or tolerance in bung position of a prefilled syringe.

Optionally, the firing mechanism comprises the first connection features and the body comprises the second connection features.

Optionally, the body comprises a rear portion and a forward portion axially moveable relative to each other, and wherein the rear portion comprises the first connection features and the forward portion comprises the second connection features.

Optionally, one of the first and second connection features comprises a thread and the other of the first and second connection features comprises a thread engagement member.

Optionally, one of the first and second connection features comprise a plurality of recesses at a plurality of axial positions, and the other of the first and second connection features comprises a lug, wherein the plurality of recesses are configured to receive the lug.

Optionally, the recesses extend laterally from an axially extending channel, and wherein lug is configured to enter one of the plurality of recesses on relative rotation between the first and second connection features.

Optionally, the injection device further comprises a retention feature on one of the plurality of recesses and/or the lug.

Optionally, the retention feature comprises biasing member configured to bias the lug towards engagement with the plurality of recesses.

Optionally, the retention feature comprises a catch on one of the plurality of recesses and/or the lug configured to engage a corresponding feature on the other of the plurality of recesses and/or the lug.

Optionally, one of the first and second connection features comprises a plurality of abutment surfaces at a plurality of axial positions, and the other of the first and second connection features comprises a further abutment surface configured to abut one of the abutment surfaces to prevent forward axial movement.

Optionally, the abutment surfaces are in a stepped arrangement, a relative rotational position of the one of the first and second connection features determining which of the plurality of abutment surfaces the further abutment surface will abut.

Optionally, the one of the first and second connection features further comprising a plurality of axial channels having a plurality of lengths, the abutment surfaces being formed by a forward end of the plurality of channels.

Optionally, the injection device further comprises a lock out device configured to lock the first and second connection features and thereby the relative axial position of the firing mechanism and the syringe locator.

Optionally, the driver system comprises a compression spring for acting, directly or indirectly, against the rear cap and the plunger to drive the plunger axially forwards with respect to the rear cap.

Optionally, the plunger is telescopically received within an axially extending elongate member of the rear cap and forms a cylinder, and wherein the compression spring is received within the plunger for acting against the rear cap and the plunger.

Optionally, the firing mechanism is located in the rear portion and the syringe locator is in the forward portion, the first and second connection features allowing adjustment of the relative axial position of the rear portion and the forward portion.

Optionally, one of the forward portion and the rear portion is telescopically received within the other of the forward portion and the rear portion.

According to the invention in an aspect, there is provided an injection device according to any described herein and comprising a syringe or safety syringe positioned within the body.

BRIEF DESCRIPTION OF THE DRAWINGS

Exemplary embodiments will be described herein with reference to the accompanying drawings, in which.

DETAILED DESCRIPTION

Generally, disclosed herein are methods and apparatus for controlling a gap between a bung of a syringe and a forward end of a plunger prior to activation of an injection device. For the remainder of this document, the term "auto-injector" will be used in place of "injection device" in order to aid description of some specific embodiments. However, this should not be seen as limiting.

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use. Further, the term axial is used to encompass a direction along or parallel to a longitudinal axis of the injection device.

Many features of the exemplary arrangements disclosed herein are described as being "coupled" to other features. This term encompasses any coupling that results in the coupled features moving together in any direction, whether that be on a 1:1 basis or on some geared basis. The term "coupled" also encompasses any one of a connection between features, an abutment of one feature against another and an engagement of one feature with another, and such coupling may be direct or may be indirect, i.e. with a third feature therebetween.

Figure 1:
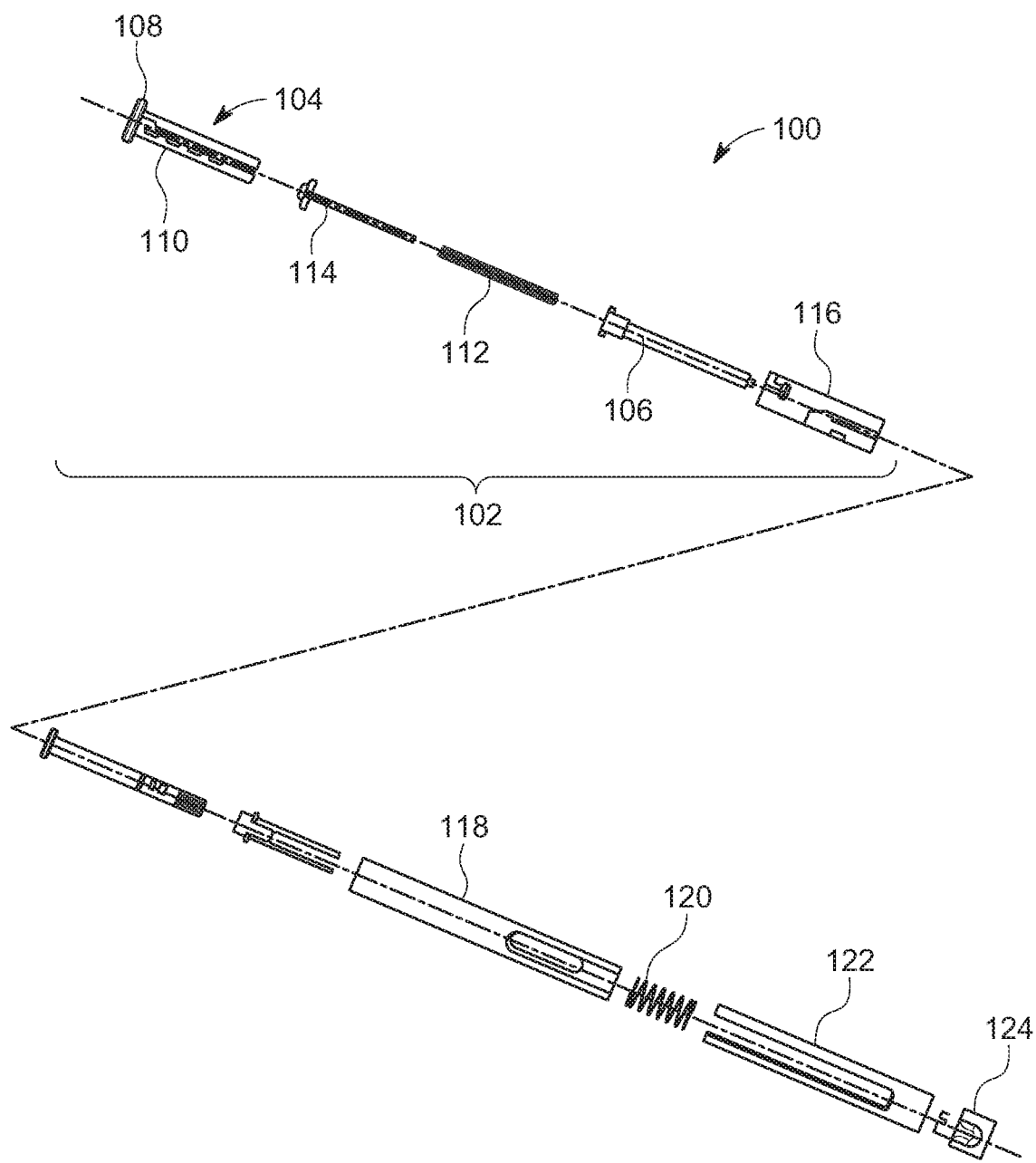
FIG. 1 is an exploded view of an auto-injector.

FIG. 1 shows an exploded view of an auto-injector 100. The auto-injector 100 comprises a firing mechanism 102. The firing mechanism 102 comprises a rear cap 104 and a plunger 106. The rear cap 104 comprises a head 108 and an elongate member 110. The rear cap 104 and the plunger 106 are connected to each other such that before firing, relative axial movement between them is resisted or prevented. The connection between the rear cap 104 and the plunger 106 is releasable such that after activation of the auto-injector 100, relative axial movement between them is permitted. The nature of the releasable connection is discussed in more detail below and may be set at assembly.

The firing mechanism 102 also comprises a biasing member 112, which forms at least part of a drive system for driving the plunger 106 axially forwards and into a barrel of a syringe (shown in FIG. 2) retained within the auto-injector 100. In one example the biasing member 112 is a drive spring (e.g. a compression spring) and will be referred to as such throughout, although this should not be construed as limiting and the skilled person will appreciate that other means may be used to drive the plunger forwards.

Figure 2:
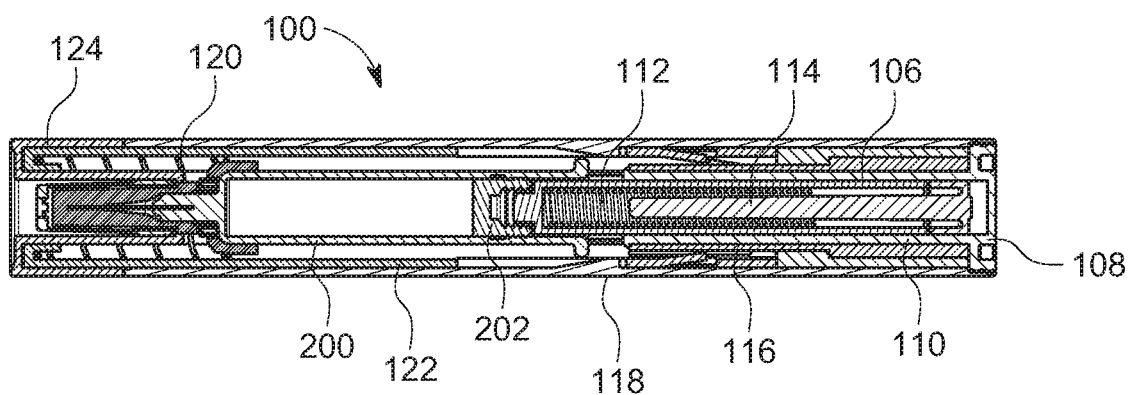
FIG. 2 is a section through an auto-injector with a syringe fitted therein.

In the example of FIG. 1, the plunger 106 is telescopically received within the elongate member 110 of the rear cap 104. The drive spring 112 is positioned between the rear cap 104 and the plunger 106 such that they are biased in opposite axial directions relative to each other. An example of this is best shown in FIG. 2, which is a section through an auto-injector 100 in an assembled state before activation and with a syringe 200 retained therein. The plunger 106 is received within the elongate member 110. The plunger is a hollow tube with an open end at the rear and the drive spring 112 is received within the plunger 106. A first end of the drive spring 112 abuts a forward end of the plunger 106 and a second end of the drive spring 112 is coupled to (i.e. abuts or is connected to) the rear cap 104 or a further member directly or indirectly axially coupled to the rear cap 104. In the example of FIG. 2, the drive spring 112 is coupled to an end of dose indicator 114, the operation of which is outside the scope of this description, and which in turn is coupled to the rear cap 104. Expansion of the drive spring 112 drives the plunger 106 forwards into the barrel of the syringe 200 because, in the example of FIG. 1, the position of the rear cap 104 is fixed.

In FIG. 2, a forward end of the plunger is shown abutting a bung 202. This will not always be the case, as discussed above.

The auto-injector 100 also comprises a clutch 116, which is positioned around the elongate member 110. Before activation of the auto-injector 100, the clutch 116 is rotationally coupled to the plunger 106. Rotation of the clutch 116 therefore causes rotation of the plunger 106. As explained below, on activation of the auto-injector 100, the clutch 116 rotates, thereby rotating the plunger 106 relative to the rear cap 104 to release the connection therebetween. Operation of the clutch 116 is explained in more detail below.

The auto-injector 100 also comprises a main body 118, which houses the firing mechanism 102, the syringe 200 and other features necessary for operation of the auto-injector 100. As discussed below, the main body 118 may comprise a plurality of separate parts. The main body 118 comprises a syringe locator, which in exemplary arrangements comprises one or more features for receiving and optionally retaining a syringe in position within the main body 118.

The auto-injector 100 also comprises a lockout spring 120 and lockout shroud 122, wherein the lockout spring 120 is configured on release thereof to displace the lockout shroud 122 axially forwards to cover a needle of the syringe. A cap 124 also forms part of the auto-injector and covers a needle or forward end of the auto-injector prior to use.

In exemplary arrangements, a rear assembly of the auto-injector may be formed from the firing mechanism 102 and a rear portion of the main body 118.

Figure 3:
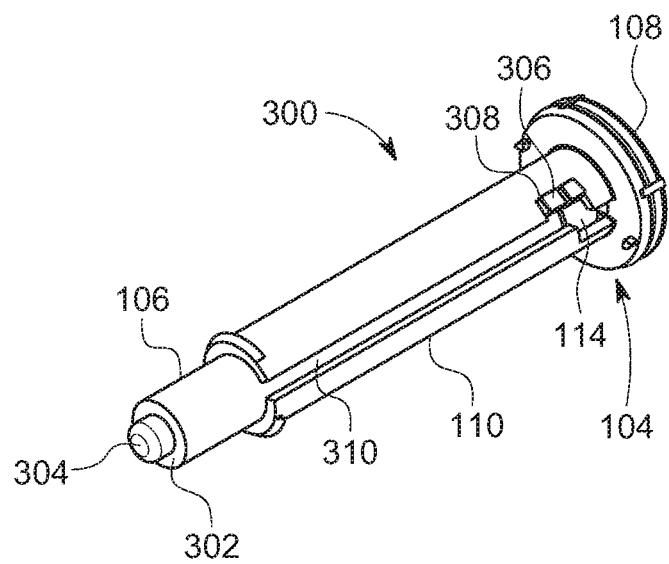
FIG. 3 is a perspective view of a firing mechanism for an injection device.

FIG. 3 shows a perspective view of an assembly 300 for a firing mechanism. The assembly 300 comprises the rear cap 104 and the plunger 106. The plunger 106 is telescopically received within the elongate member 110. The assembly 300 may also comprise an end of dose indicator 114, but as explained above, the operation of that feature is beyond the scope of this description.

The exemplary plunger 106 comprises a cylindrical tube that is open at a rear end and closed at a forward end. The forward end of the plunger 106 comprises a shoulder 302 and a projection 304 configured to engage a bung 202 in a syringe barrel. In the example shown in FIG. 3, the plunger 106 also comprises a plunger release lug 306 configured to engage with a plunger release recess 308 in the elongate member 110. In the exemplary arrangements of FIG. 3 the lug 306 extends radially from an outer surface of the plunger 106.

The elongate member 110 comprises an axially extending plunger release channel 310. The recess 308 is formed in a sidewall of the channel 310. That is, the recess 308 extends circumferentially (or transverse to the axial channel) around the outer of the elongate member 110. It is noted that while only one recess 308 is shown in FIG. 3, more recesses may be provided in the elongate member 110 at different axial positions. The recess 308 is configured to receive the lug 306 of the plunger 106. FIG. 3 shows the lug 306 received in the recess 308.

The axial channel 310 and the recess 308 are configured such that rotation of the plunger 106 relative to the elongate member 110 in a first direction moves the lug 306 into the recess 308 and rotation in a second, opposite direction moves the lug 306 out of the recess 308. As discussed above, rotation of the plunger 106 may be provided by rotation of the clutch 116, which is rotationally coupled to the plunger 106.

Figure 4A:
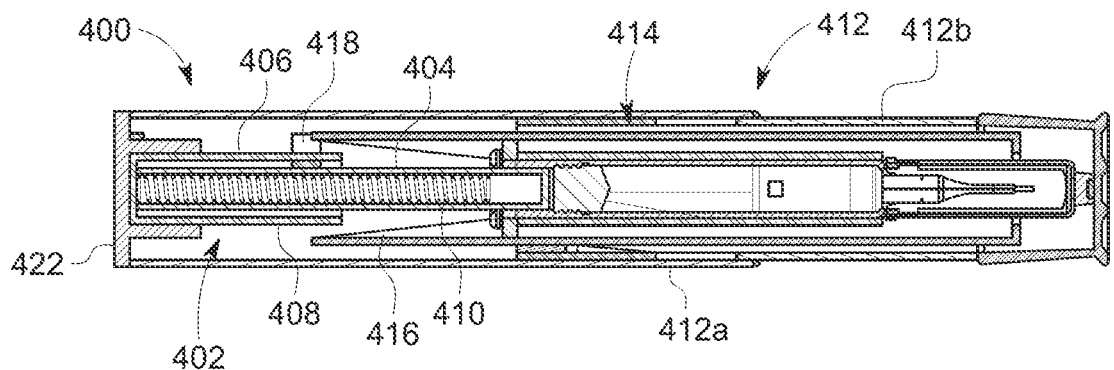
FIGS. 4 to 7 are schematic representations of exemplary rear assemblies.
Figure 4B:
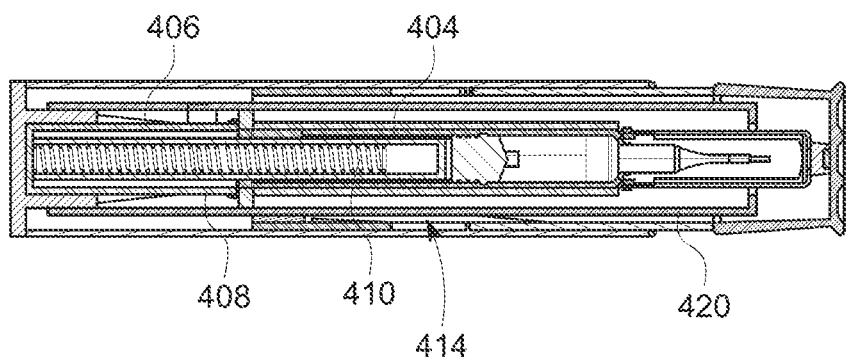

FIGS. 4a and 4b show a schematic representation of a section through an injection device 400. The exemplary arrangement of FIGS. 4a and 4b allow for the connection of the firing mechanism to the body to be controlled to allow adjustment of a relative axial position between the firing mechanism, and more specifically a forward end of the plunger rod, and the syringe locator during assembly of the injection device. This controls a start position of the forward end of the plunger on activation of the injection device 400. Specifically, when a syringe is fitted to the injection device, the start position of the forward end of the plunger relative to the bung of the syringe is controlled.

The injection device 400 comprises a firing mechanism 402. The firing mechanism 402 may comprise one or more of the features of the firing mechanism 300 shown in FIG. 3 and described above. As shown in FIG. 4, the firing mechanism 402 comprises a plunger 404 and a rear cap 406. The rear cap comprises an elongate member 408 into which the plunger 404 is telescopically received. A drive spring 410 is received within the plunger 404 and acts against in opposed directions the plunger 404 and the rear cap 406. The skilled person will appreciate that the specific firing mechanism configuration shown in FIG. 4 is not essential to the invention and that other firing assemblies may be used.

In the arrangement of FIGS. 4a and 4b (and indeed of FIGS. 5 to 7), the firing mechanism 402 is connected to a rear portion 412a a body 412 and the syringe locator (and therefore the syringe, when in use) is connected to or forms part of a forward portion 412b of the body 412.

In the example, the firing mechanism 402 is in fixed connection with the rear portion 412a after assembly and optionally there is only a single connection point. That is, in the example shown the firing mechanism 402 is always assembled in the same relative axial position to the rear body 412a. However, it will be understood by the skilled person that the features of any other embodiment described herein may be incorporated into the arrangement of FIGS. 4a and 4b, as appropriate. Accordingly, the axial position of the firing mechanism 402 within the rear portion 412a may be controlled as set out herein and this may be in combination with the features described below.

The relative axial position of the firing mechanism 402 in the rear portion 412a to the syringe locator in the forward portion 412b is controlled by first and second connection features, which in this example comprise a threaded connection 414 between the rear portion 412a and the forward portion 412b. That is, one of the first and second connection features comprises a thread and the other of the first and second features comprises a thread engagement member, which may be a lug or another, corresponding thread.

In FIG. 4, the first and second connection features are located on the forward and rear portions 412a, 412b of the body 412. In other arrangements, one of the first and second connection features may be located on the rear portion 412b of the body 412, and the other of the first and second connection features may be located on the firing mechanism. This is generally true of the exemplary arrangements in FIGS. 5-7 also.

The threaded connection 414 comprises a thread on the rear portion 412b and a corresponding thread engagement feature on the forward portion 412a. The skilled person will appreciate that these may be oppositely configured.

The forward portion 412b is telescopically received within the rear portion 412a (although this may be oppositely configured) and the distance by which it is received is controlled by the threaded connection 414.

FIG. 4a shows the forward portion 412b received within the rear portion 412a by a first distance, and FIG. 4b shows the forward portion 412b received within the rear portion 412a by a second distance greater than the first distance. This is achieved by increased rotation of the rear portion 412b relative to the forward portion 412a and the corresponding. This allows control of the relative axial distance between the firing mechanism 402 and a syringe located within the syringe locator. The arrangement of FIG. 4b has a reduced axial distance between the two when compared to the axial distance shown in FIG. 4a.

As with the exemplary arrangement of FIGS. 6a-c and 7a-c described below, the sheath 420 may comprise an angled surface 416 to interact with a lug 418 of the plunger 404 to displace it laterally at any axial position, based on the configuration of the threaded connection 414. Accordingly, the rotational alignment of the firing mechanism 402, and therefore the lug 418, may be controllable. For example, an end blank 422 may be rotatable and rotationally coupled to the firing mechanism 402 to select a rotational alignment of the firing mechanism 402 relative to the body 412 and therefore the sheath 420. Alternatively, a clutch arrangement may be used as described herein.

Figure 5:
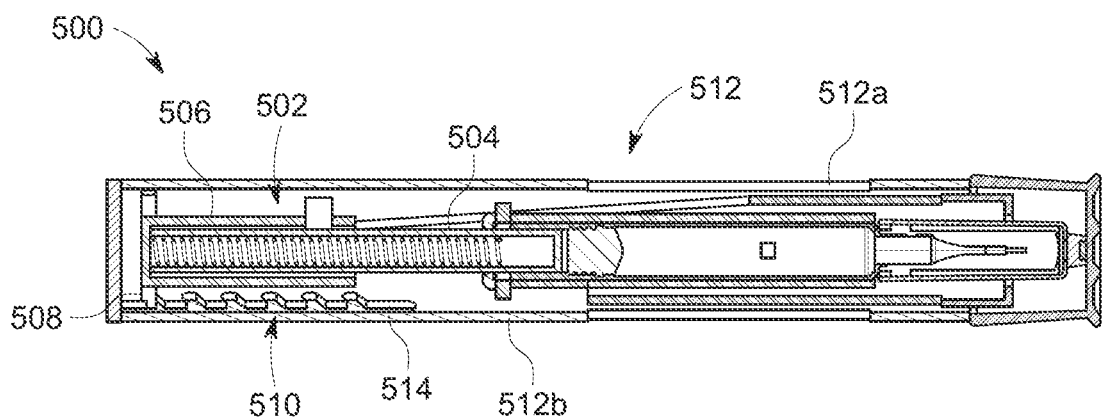

FIG. 5 shows an alternative arrangement of an injection device 500 allowing the connection of the firing mechanism to the body to be set at one of a plurality of relative axial alignments during assembly of the injection device. This in turn allows adjustment or control over a relative axial position of the firing mechanism and the syringe locator.

A firing mechanism 502 is shown only schematically, although the arrangements disclosed above may be used. The firing mechanism 502 comprises a plunger 504 and a rear cap 506. The rear cap 506 comprises one or more lugs 508. The lug 508 extends radially outwards. A body 512 comprises a forward portion 512a and a rear portion 512b. In the example of FIG. 5, the rear portion 512b comprises first connection features, which further comprise a plurality of recesses 510 at a plurality of axial positions on the body. The recesses 510 are configured to receive second connection features, which comprise the one or more lugs 508 to prevent relative axial movement between the firing mechanism 502 and the body 512. In the example shown in FIG. 5, the recesses 510 extend laterally on an inner wall of the body 512. That is, the recesses 510 extend transverse to the axial direction of the injection device 500. In such arrangements, the lug 508 may enter one of the recesses 510 on relative rotation of the firing mechanism 502 and the body 512.

In the example shown in FIG. 5, the body 512 also comprises an axial channel 514 from which the recesses 510 extend. The axial channel 514 is configured to receive the lug 508 and allow axial movement of the firing mechanism 502.

In addition, the recesses 510 and/or the lug 508 may include a retention feature. The retention feature may retain the lug 508 in the recess 510 into which it has entered. The retention feature may take any of a number of forms, such as a snap fit arrangement, a catch and/or a biasing member configured to bias the lug 508 towards the recess 510, optionally in cooperation with one or more angled surfaces.

On assembly of the injection device, the firing mechanism 502 is received within the body 512 until the lug 508 is received within the channel 514 and moved axially until it is aligned with a selected one of the recesses 510. The firing mechanism 502 is then rotated relative to the body 512 to cause the lug 508 to enter the recess 510.

In an alternative arrangement, the second connection features comprise one or more sprung lugs and the first connection features comprise a plurality if recesses at different axial positions. The sprung lugs may be configured to ride over the body until they are located within the correct recess.

In a further embodiment, the forward portion 512a may be telescopically received within the rear portion 512a and the second connection feature (i.e. the lug 508) may be positioned on the forward portion 512b as opposed to the firing assembly 502. The second connection feature (i.e. the channel 514 and the recesses 510) are located on the rear portion 512b and are configured to engage with the lug 508 on the forward portion 512a and may therefore be positioned forwards of the position shown in FIG. 5 and optionally at a forward end of the rear portion 512b. The position of the firing assembly 502 within the rear portion 512b may be fixed. This arrangement is similar to the arrangement of FIGS. 4, 6 and 7, except that the connection between the forward portion 512a and the rear portion 512b is controlled by receipt of the lug 508, which is formed on the forward portion 512a, within the channel 510 and subsequently one of the recesses 510.

Figure 6A:
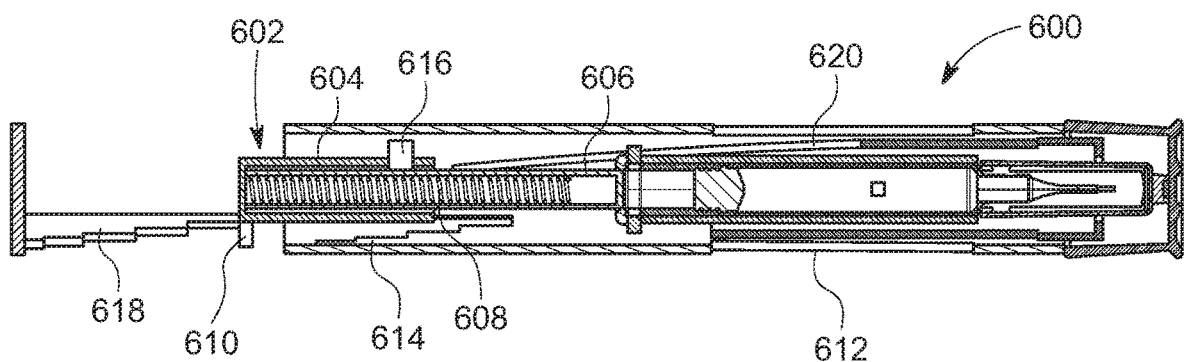
Figure 6B:
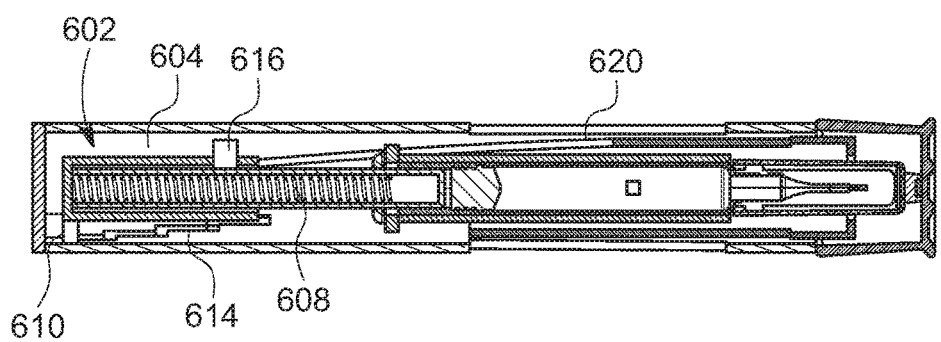
Figure 6C:
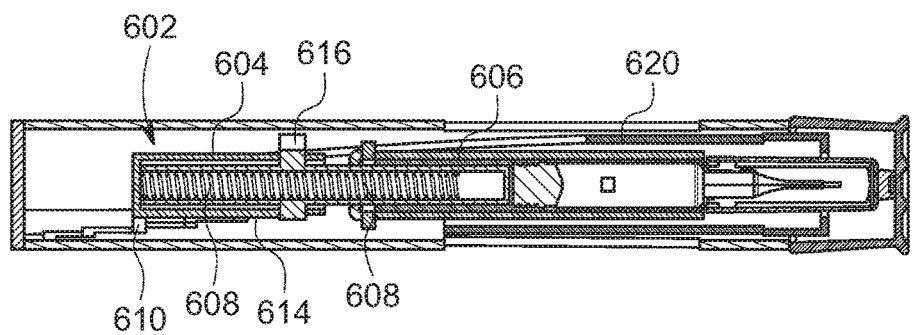

FIGS. 6a-c show a further exemplary arrangement of an injection device 600. The injection device 600 is configured to allow the connection of a firing mechanism to a body to be set at one of a plurality of relative axial alignments during assembly of the injection device.

In the exemplary arrangement of FIG. 6, the firing mechanism 602 comprises a rear cap 604, a plunger 606 and a drive system, which in this case comprises a compression spring 608. The rear cap 604 is configured to retain the plunger 606 against a bias applied by the compression spring 608, such retention being releasable on operation on the injection device 600, as explained above. First connection features comprise a guide member 610 located on the firing mechanism 602 and that is configured to align with second connection features, which comprise corresponding guide features on a body 612 of the injection device 600. The guide features 614 on the body 612 comprise a plurality of abutment surfaces, each at different axial locations on the body 612. In the example shown in FIG. 6, the abutment surfaces for a stepped arrangement. The guide feature 610 of the firing mechanism 602 comprises a protrusion from the rear cap 604, although other forms of guide feature are possible.

During assembly, the firing mechanism 602 is located within the body 612. The rotational alignment of the firing mechanism 602 relative to the body 612 determines which of the abutment surfaces the guide feature 610 of the firing mechanism 602 will rest on. In FIG. 6b, the guide feature 610 rests on a first abutment surface and in FIG. 6c, the guide feature 610 rests on a second abutment surface further forward than the first abutment surface. Therefore, the relative axial position of the firing mechanism 602 and the syringe locator of the body 612 may be controlled.

The injection device 600 also comprises an end blank 618 that may be fitted into a rear end of the device after location of the firing mechanism 602. The end blank 618 comprises a plurality of features configured to align with the guide features 614 of the body 612. The end blank 618 retains the firing mechanism 602 in the selected axial position.

In the example of FIGS. 6a-c, the plunger 606 comprises a lug 616 that is located in a recess of the rear cap 604 while the plunger 606 is being retained. Relative rotation between the plunger 606 and the rear cap 604 disengages the lug 616 from the recess and allows the compression spring 608 to drive the plunger 606 forwards. In the example shown in FIGS. 6a-c, the sheath 620 may be configured to cause that relative rotation of the plunger 606. In specific examples, the sheath 620 may comprise an angled surface configured to displace the lug 616 laterally on rearward displacement of the sheath 620. As can be seen in FIGS. 6b and 6c, the axial position of the lug may be changed with the axial position of the firing mechanism 602. Therefore, the sheath 620 may be configured to laterally displace the lug 616 at each of the possible axial positions. Accordingly, the angled surface of the sheath 620 may be arranged to interact with the lug at different axial positions and also at different rotational alignments with the sheath 620 (and the body 612). That is, as the firing mechanism 602 is rotated to abut the correct abutment surface, the rotational position of the lug 616 is altered. Therefore, the angled surface of the sheath 620 may be configured to displace the lug 616 at different axial positions based on the rotational position of the lug 616. In some arrangements, the sheath 620 may comprise a plurality of angled surfaces corresponding to the abutment surfaces, wherein each angled surface is configured to displace the lug 616 laterally when the guide feature 610 of the firing mechanism 602 abuts one of the abutment surfaces. In other arrangements, a clutch may be used, as described herein, wherein the clutch is coupled to the sheath 620 such that rearward axial displacement of the sheath causes rotation of the clutch irrespective of the axial position of the firing mechanism 602. The clutch may be rotationally coupled to the syringe plunger to cause lateral displacement of the lug 616.

Figure 7A:
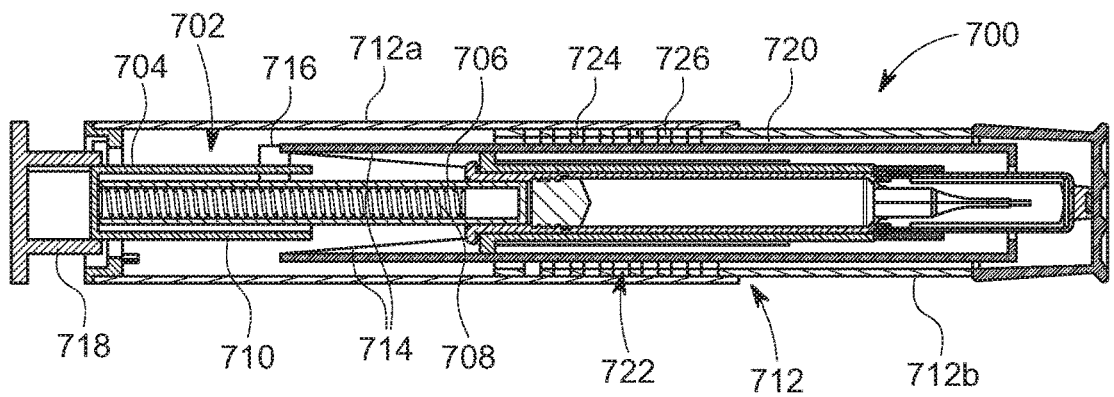
Figure 7B:
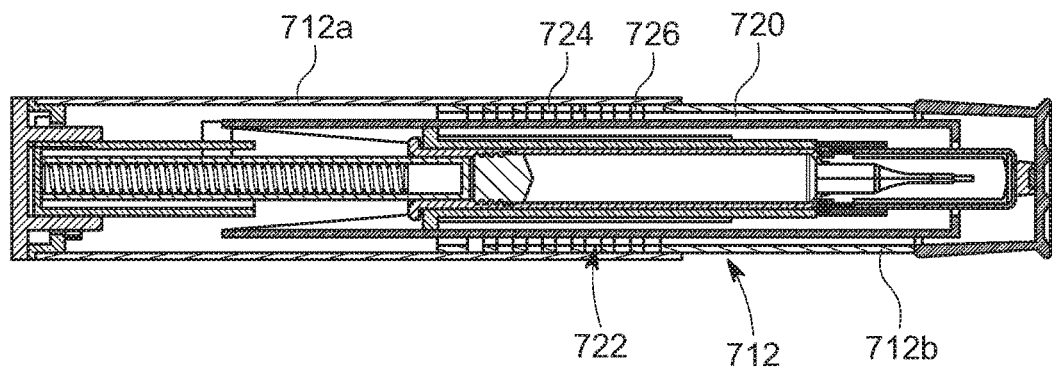
Figure 7C:
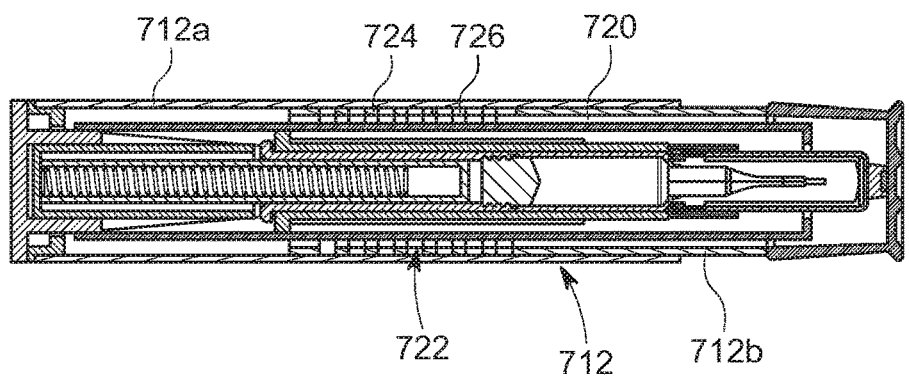

FIGS. 7a-c show a further exemplary injection device 700. In the exemplary arrangement of FIGS. 7a-c, a firing mechanism 702 comprises a rear cap 704, a plunger 706 and a drive system, which in this case comprises a compression spring 708. The rear cap 704 is configured to retain the plunger 706 against a bias applied by the compression spring 708, such retention being releasable on operation on the injection device 700, as explained above. In the arrangement of FIGS. 7a-c, the firing mechanism 702 is connected to a rear portion 712a of the body 712 and the syringe locator (and therefore the syringe, when in use) is connected to or forms part of a forward portion 712b of the body 712.

In the example, of FIGS. 7a-c, the firing mechanism 702 is in fixed connection with the rear portion 712a after assembly and there is only a single connection point. That is, the firing mechanism 702 is always assembled in the same relative axial position to the rear body 712a. However, it will be understood by the skilled person that the features of any other embodiment described herein may be incorporated into the arrangement of FIGS. 7a-c, as appropriate. Accordingly, the axial position of the firing mechanism 702 within the rear portion 712a may be controlled as set out herein and this may be in combination with the features described below.

The relative axial position of the firing mechanism 702 in the rear portion 712a to the syringe locator in the forward portion 712b is controlled by first and second connection features 722 on the body 712 that allow control of the relative axial position of the rear portion 712a to the forward portion 712b. The connection features 722 comprise first connection features 722a that are configured to cooperate with second connection features 722b.

The rear portion connection features 722a comprise at least one internal protrusion 724 that is configured to be received with any of a plurality of recesses 726 forming part of the rear portion connection features 722b. It will be understood that the at least one internal protrusion and the recesses may be on one or both of the rear portion 712a and the forward portion 712b. In the exemplary arrangement of FIGS. 7a-c, each of the rear portion connection features 722a and the forward portion connection features 722b comprises a plurality of internal protrusions 724 and a plurality of recesses 726. Further, the protrusions and recesses extend at least partially, and in one arrangement fully, around an inner circumference of the rear portion 712a and an outer circumference of the forward portion 712b.

The forward portion 712b is telescopically received within the rear portion 712a (although this may be oppositely configured) and the distance by which it is received is controlled by the connection features 722.

FIG. 7b shows the forward portion 712b received within the rear portion 712a by a first distance, and FIG. 7c shows the forward portion 712b received within the rear portion 712a by a second distance greater than the first distance. This allows control of the relative axial distance between the firing mechanism 702 and a syringe located within the syringe locator. The arrangement of FIG. 7c has a reduced axial distance between the two when compared to the axial distance shown in FIG. 7b.

The skilled person will be able to envisage a number of other connection features to connect the rear portion 712a to the forward portion 712b and the example given in FIGS. 7a-c is not limiting. For example, the connection features may comprise a threaded arrangement on the rear portion 712a and the forward portion 712b. Alternatively, the connection features may comprise sprung loaded protrusions and a plurality of recesses. The above are merely examples and should not be construed as limiting.

As with the exemplary arrangement of FIGS. 6a-c, the sheath 720 may comprise an angled surface 714 to interact with a lug 716 of the plunger 706 to displace it laterally at a plurality of axial positions, based on the configuration of the connection features 722a, 722b. Accordingly, the rotational alignment of the firing mechanism, and therefore the lug 716, may be controllable. For example, an end blank 718 may be rotatable and rotationally coupled to the firing mechanism 702 to select a rotational alignment of the firing mechanism 702 relative to the body 712 and therefore the sheath 720. Alternatively, a clutch arrangement may be used as described herein.

Once assembled, the user has no control over the relative axial position of the firing mechanism compared to the body. Any of the rear assemblies disclosed herein may also comprise a lock that may be activated to lock the axial position of the rear cap relative to the body.

Operation of the auto-injector 100 is described below using the reference numerals of the exemplary arrangement shown in FIGS. 1 and 2. Any of the arrangements of the rear assembly described above may be used.

In use, a user removes the cap 124 of the auto-injector 100, which in turn removes a rigid needle shield covering the needle. Removal of the cap exposes the lockout shroud 122, which protrudes from a forward end of the body 118.

The user places a forward end of the lockout shroud 122 against an injection site and pushes the auto-injector 100 downwards onto the injection site. This action pushes the lockout shroud 122 rearwards within the auto-injector 100. The lockout shroud interacts with the clutch 116 to rotate it. This may be done by forcing a surface (or pip) of the lockout shroud 122 against an angled surface on the clutch 116, which translates the rearward motion of the lockout shroud 122 into rotational motion of the clutch 116.

As the clutch 116 is rotationally coupled to the plunger 106, rotation of the clutch 116 causes rotation of the plunger 106. In some arrangements, the clutch 116 may have an internal track located on an internal wall thereof and that receives a lug of the plunger 106. The lug may be the same as the lug 306 described with reference to FIG. 3. Rotation of the plunger 106 with respect to the rear cap 104 releases the connection between the rear cap 104 and the plunger 106, allowing the plunger 106 to be driven forwards under force of the drive spring 112. In the examples of FIGS. 1-3, this is provided by rotating the lug 306 of the plunger 106 out of the recess 308 the lug 306 is positioned in at assembly and into the axial channel 310. The lug 306 is thereby allowed to travel forwards within the channel 310.

The drive spring 112 then acts against the plunger 106 and the rear cap 104. Because the rear cap 104 is fixed within the auto-injector 100, the force delivered by the drive spring 112 acts to drive the plunger 106 into the barrel of the syringe. Because the gap between the forward end of the plunger 106 and the bung 202 has been controlled during assembly, the plunger 106 does not accelerate above a safe velocity that would risk damage to the syringe 200 or harm or discomfort to the subject of the injection.

After delivery of the contents of the syringe 200, the lockout shroud is deployed under force of the lockout spring 120 in any of a number of ways that will be apparent to the skilled person.

The skilled person will be able to envisage other assemblies, auto-injectors and features thereof without departing from the scope of the appended claims. In particular, it is noted that one or more features included in one or more drawings may be integrated into auto-injectors shown in other drawings, as will be appreciated by the skilled person.

The invention claimed is:

1. An injection device comprising:
a body comprising a syringe locator for receiving a syringe; and
a firing mechanism configured to deliver a fluid from the syringe, the firing mechanism comprising a rear cap, a plunger configured to be axially displaced in a forward direction relative to the rear cap and a driver system for driving the plunger forwards upon activation of the injection device, the firing mechanism configured to be directly or indirectly connected to the body such that an axial spacing of the rear cap and a barrel of the syringe is fixed during operation of the injection device,
wherein, the firing mechanism and/or the body comprise first and second connection features allowing adjustment of a relative axial position of the firing mechanism and the syringe locator during assembly of the injection device.

2. The injection device according to claim 1, wherein the firing mechanism comprises the first connection features and the body comprises the second connection features.

3. The injection device according to claim 2, wherein one of the first and second connection features comprises a thread and the other of the first and second connection features comprises a thread engagement member.

4. The injection device according to claim 2, wherein the rear cap comprises the first connection features.

5. The injection device according to claim 2, wherein the body comprises a rear portion and a forward portion, and wherein the rear portion comprises the second connection features.

6. The injection device according to claim 1, wherein the body comprises a rear portion and a forward portion axially moveable relative to each other, and wherein the rear portion comprises the first connection features and the forward portion comprises the second connection features.

7. An injection device according to claim 6, wherein the firing mechanism is located in the rear portion and the syringe locator is in the forward portion, the first and second connection features allowing adjustment of the relative axial position of the rear portion and the forward portion.

8. The injection device according to claim 7, wherein one of the forward portion and the rear portion is telescopically received within the other of the forward portion and the rear portion.

9. The injection device according to claim 6, wherein one of the first and second connection features comprises a thread and the other of the first and second connection features comprises a thread engagement member.

10. The injection device according to claim 1, wherein one of the first and second connection features comprises a thread and the other of the first and second connection features comprises a thread engagement member.

11. The injection device according to claim 1, wherein one of the first and second connection features comprise a plurality of recesses at a plurality of axial positions, and the other of the first and second connection features comprises a lug, wherein the plurality of recesses are configured to receive the lug.

12. The injection device according to claim 11, wherein the recesses extend laterally from an axially extending channel,
and wherein the lug is configured to enter one of the plurality of recesses on relative rotation between the first and second connection features.

13. The injection device according to claim 11, further comprising a retention feature on one of the plurality of recesses and/or the lug.

14. The injection device according to claim 13, wherein the retention feature comprises a catch on one of the plurality of recesses and/or the lug configured to engage a corresponding feature on the other of the plurality of recesses and/or the lug.

15. The injection device according to claim 11, wherein receipt of the lug in one of the plurality of recesses prevents relative axial movement between the firing mechanism and the body.

16. The injection device according to claim 1, wherein one of the first and second connection features comprises a plurality of abutment surfaces at a plurality of axial positions, and the other of the first and second connection features comprises a further abutment surface configured to abut one of the abutment surfaces to prevent forward axial movement.

17. The injection device according to claim 16, wherein the abutment surfaces are in a stepped arrangement, a relative rotational position of the one of the first and second connection features determining which of the plurality of abutment surfaces the further abutment surface will abut.

18. The injection device according to claim 16, the one of the first and second connection features further comprising a plurality of axial channels having a plurality of lengths, the abutment surfaces being formed by a forward end of the plurality of channels.

19. The injection device according to claim 1, further comprising a lock out device configured to lock the first and second connection features and thereby the relative axial position of the firing mechanism and the syringe locator.

20. The injection device according to claim 1, wherein the driver system comprises a compression spring for acting, directly or indirectly, against the rear cap and the plunger to drive the plunger axially forwards with respect to the rear cap.

21. The injection device according to claim 20, wherein the plunger is telescopically received within an axially extending elongate member of the rear cap and forms a cylinder, and wherein the compression spring is received within the plunger for acting against the rear cap and the plunger.

22. The injection device according to claim 1 further comprising a syringe positioned within the body.

23. The injection device according to claim 1, wherein the driver system is configured to push against the rear cap to drive the plunger forwards upon activation of the injection device.

\* \* \* \* \*